(12) United States Patent
Strauss et al.

(10) Patent No.: US 9,681,863 B2
(45) Date of Patent: Jun. 20, 2017

(54) MINIMALLY OPEN RETRACTION DEVICE

(71) Applicant: K2M, Inc., Leesburg, VA (US)

(72) Inventors: Kevin R. Strauss, Columbia, MD (US); Josef Gorek, Ross, CA (US); Larry McClintock, Gore, VA (US); John Kostuik, Baltimore, MD (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 14/833,609

(22) Filed: Aug. 24, 2015

(65) Prior Publication Data

US 2015/0359528 A1 Dec. 17, 2015

Related U.S. Application Data

(62) Division of application No. 14/228,639, filed on Mar. 28, 2014, now Pat. No. 9,131,934, which is a division of application No. 11/799,576, filed on May 2, 2007, now Pat. No. 8,696,560.

(51) Int. Cl.
| | | |
|---|---|---|
| *A61B 17/02* | (2006.01) | |
| *A61B 1/32* | (2006.01) | |
| *A61B 17/70* | (2006.01) | |

(52) U.S. Cl.
CPC ............ *A61B 17/0218* (2013.01); *A61B 1/32* (2013.01); *A61B 17/02* (2013.01); *A61B 17/0293* (2013.01); *A61B 17/7083* (2013.01); *A61B 17/7001* (2013.01); *A61B 17/7032* (2013.01); *A61B 2017/0225* (2013.01)

(58) Field of Classification Search
CPC . A61B 17/02; A61B 17/0206; A61B 17/0218; A61B 17/025; A61B 17/0293; A61B 2017/0225; A61B 2017/0256; A61B 2017/0262; A61B 2017/0287
See application file for complete search history.

(56) References Cited

U.S. PATENT DOCUMENTS

| | | | |
|---|---|---|---|
| 196,600 A | 10/1877 | Shiland | |
| 2,701,562 A | 2/1955 | Sidney et al. | |
| 3,129,706 A | 4/1964 | Reynolds | |
| 3,192,928 A | 7/1965 | Horton | |
| 3,766,910 A * | 10/1973 | Lake | A61B 17/0206 600/213 |
| 4,421,107 A * | 12/1983 | Estes | A61B 17/0293 600/206 |
| 4,957,495 A * | 9/1990 | Kluger | A61B 17/7077 606/258 |
| 4,966,130 A | 10/1990 | Montaldi | |
| 5,242,443 A | 9/1993 | Kambin | |

(Continued)

*Primary Examiner* — Matthew Lawson
*Assistant Examiner* — Amy Sipp
(74) *Attorney, Agent, or Firm* — Carter, DeLuca, Farrell & Schmidt, LLP

(57) ABSTRACT

A retractor having a pair of blades is disclosed. A ring having an opening is attached to one end of the blades. The blades define a channel therebetween. The blades may be pivotally coupled to the ring. The retractor may have at least two conditions. In a first condition, the retractor is insertable through an incision in a patient's skin to an operative site. In a second condition, the retractor may be manipulated for retracting tissue surrounding the operative site. Instruments, prostheses, or tissue may be inserted or removed through the channel of the retractor.

20 Claims, 11 Drawing Sheets

(56) References Cited

U.S. PATENT DOCUMENTS

| | | | |
|---|---|---|---|
| 5,291,901 A * | 3/1994 | Graf | A61B 5/103 33/512 |
| 5,582,577 A | 12/1996 | Lund et al. | |
| 5,718,705 A * | 2/1998 | Sammarco | A61B 17/8863 606/260 |
| 5,769,783 A | 6/1998 | Fowler | |
| 5,902,231 A | 5/1999 | Foley et al. | |
| 5,928,139 A * | 7/1999 | Koros | A61B 17/0206 600/205 |
| 5,944,658 A | 8/1999 | Koros et al. | |
| 5,947,896 A | 9/1999 | Sherts et al. | |
| 5,976,146 A | 11/1999 | Ogawa et al. | |
| 6,099,547 A | 8/2000 | Gellman et al. | |
| 6,132,464 A * | 10/2000 | Martin | A61F 2/4405 606/248 |
| 6,187,000 B1 | 2/2001 | Davison et al. | |
| 6,200,322 B1 | 3/2001 | Branch et al. | |
| 6,206,826 B1 | 3/2001 | Mathews et al. | |
| 6,360,750 B1 | 3/2002 | Gerber et al. | |
| 6,447,512 B1 * | 9/2002 | Landry | A61B 17/1757 606/279 |
| 6,530,926 B1 | 3/2003 | Davison | |
| 6,530,929 B1 | 3/2003 | Justis et al. | |
| 6,616,605 B2 | 9/2003 | Wright et al. | |
| 6,743,206 B1 | 6/2004 | Smith et al. | |
| 6,796,422 B1 | 9/2004 | Lu | |
| 6,800,084 B2 | 10/2004 | Davison et al. | |
| 6,849,064 B2 | 2/2005 | Hamada | |
| 6,929,606 B2 | 8/2005 | Ritland | |
| 7,008,422 B2 | 3/2006 | Foley et al. | |
| 7,011,660 B2 | 3/2006 | Sherman et al. | |
| 7,056,321 B2 | 6/2006 | Pagliuca et al. | |
| 7,083,621 B2 | 8/2006 | Shaolian et al. | |
| 7,108,705 B2 | 9/2006 | Davison et al. | |
| 7,144,393 B2 | 12/2006 | DiPoto et al. | |
| 7,160,300 B2 | 1/2007 | Jackson | |
| 7,166,107 B2 | 1/2007 | Anderson | |
| 7,179,261 B2 | 2/2007 | Sicvol et al. | |
| 7,188,626 B2 | 3/2007 | Foley et al. | |
| 7,250,052 B2 | 7/2007 | Landry et al. | |
| 7,396,360 B2 * | 7/2008 | Lieberman | A61B 17/1757 606/104 |
| 7,537,564 B2 | 5/2009 | Bonadio et al. | |
| 7,588,575 B2 | 9/2009 | Colleran et al. | |
| 7,618,442 B2 | 11/2009 | Spitler et al. | |
| 7,758,584 B2 | 7/2010 | Bankoski et al. | |
| 7,879,074 B2 | 2/2011 | Kwak et al. | |
| 8,012,182 B2 | 9/2011 | Couedic et al. | |
| 8,043,343 B2 | 10/2011 | Miller et al. | |
| 8,097,027 B2 | 1/2012 | Lim et al. | |
| 8,118,840 B2 | 2/2012 | Trieu et al. | |
| 8,231,528 B1 | 7/2012 | Friedrich et al. | |
| 8,251,901 B2 | 8/2012 | White et al. | |
| 8,398,644 B2 | 3/2013 | Kirschman | |
| 8,556,905 B2 | 10/2013 | Simonson | |
| 2003/0004401 A1 | 1/2003 | Ball et al. | |
| 2003/0149341 A1 * | 8/2003 | Clifton | A61B 17/0206 600/210 |
| 2003/0171749 A1 | 9/2003 | Le Couedic et al. | |
| 2003/0191371 A1 | 10/2003 | Smith et al. | |
| 2003/0208203 A1 | 11/2003 | Lim et al. | |
| 2005/0065517 A1 * | 3/2005 | Chin | A61B 17/3421 606/86 A |
| 2005/0165408 A1 | 7/2005 | Puno et al. | |
| 2005/0228376 A1 | 10/2005 | Boomer et al. | |
| 2006/0079894 A1 | 4/2006 | Colleran et al. | |
| 2006/0173454 A1 | 8/2006 | Spitler et al. | |
| 2006/0206009 A1 * | 9/2006 | Von Wald | A61B 17/02 600/231 |
| 2006/0229614 A1 | 10/2006 | Foley et al. | |
| 2006/0247645 A1 * | 11/2006 | Wilcox | A61B 17/025 606/86 R |
| 2006/0264962 A1 | 11/2006 | Chin et al. | |
| 2006/0271057 A1 | 11/2006 | Shluzas et al. | |
| 2007/0055247 A1 | 3/2007 | Jahng | |
| 2007/0106123 A1 | 5/2007 | Gorek et al. | |
| 2007/0129731 A1 | 6/2007 | Sicvol et al. | |
| 2007/0156023 A1 | 7/2007 | Frasier et al. | |
| 2007/0167954 A1 | 7/2007 | Sicvol et al. | |
| 2007/0270842 A1 | 11/2007 | Bankoski et al. | |
| 2008/0214898 A1 * | 9/2008 | Warren | A61B 17/02 600/210 |
| 2008/0262318 A1 | 10/2008 | Gorek et al. | |
| 2009/0093684 A1 | 4/2009 | Schorer | |
| 2009/0099605 A1 | 4/2009 | Fallin et al. | |
| 2009/0131755 A1 | 5/2009 | White et al. | |
| 2009/0222044 A1 | 9/2009 | Gorek | |
| 2009/0222046 A1 | 9/2009 | Gorek | |
| 2011/0130634 A1 | 6/2011 | Solitario, Jr. et al. | |
| 2012/0123432 A1 | 5/2012 | Kirschman | |
| 2012/0190934 A1 | 7/2012 | Gorek et al. | |
| 2012/0232350 A1 | 9/2012 | Seex | |
| 2013/0158611 A1 | 6/2013 | Kirschman | |
| 2013/0245383 A1 | 9/2013 | Friedrich et al. | |
| 2013/0245384 A1 | 9/2013 | Friedrich et al. | |

* cited by examiner

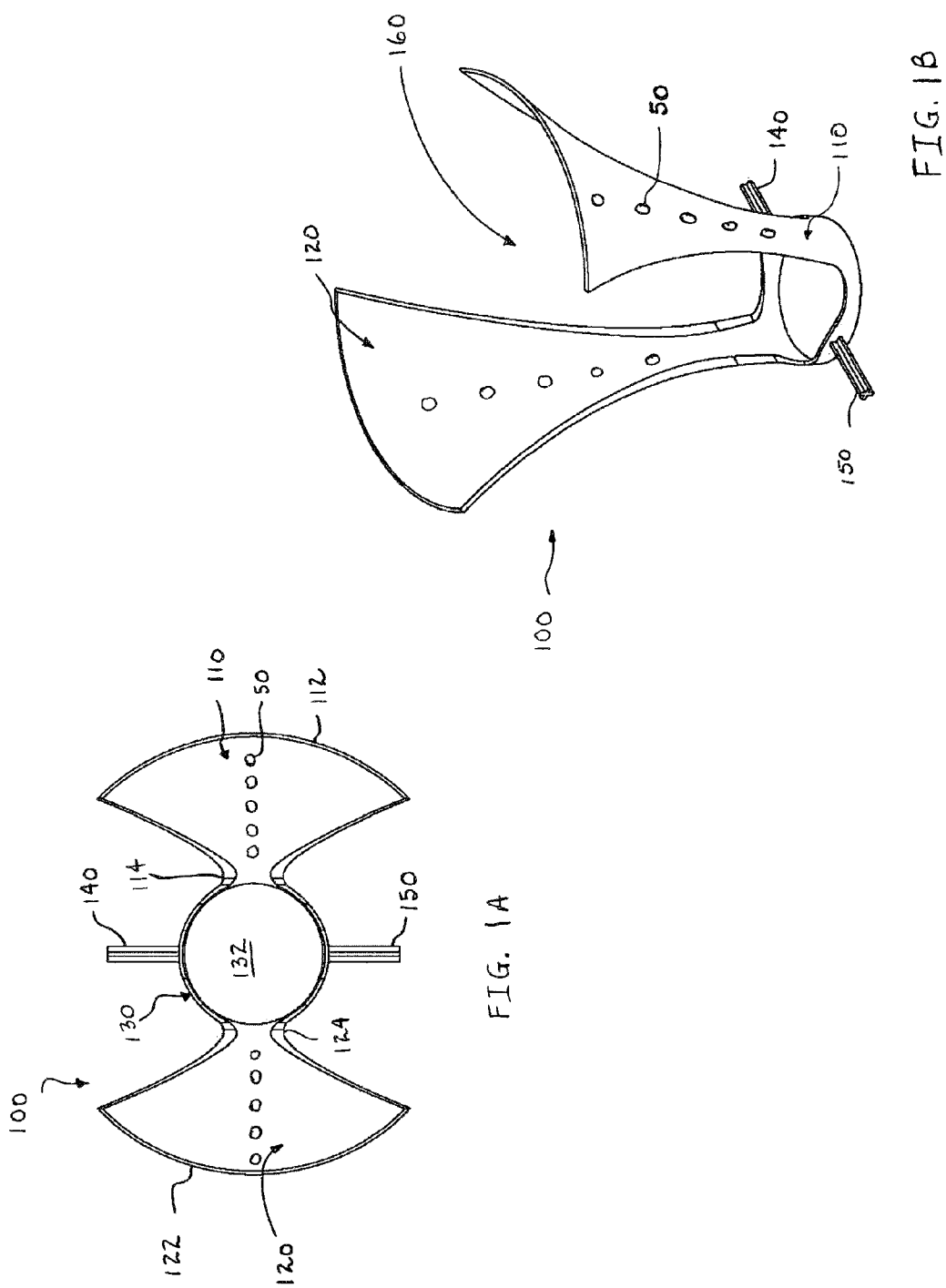

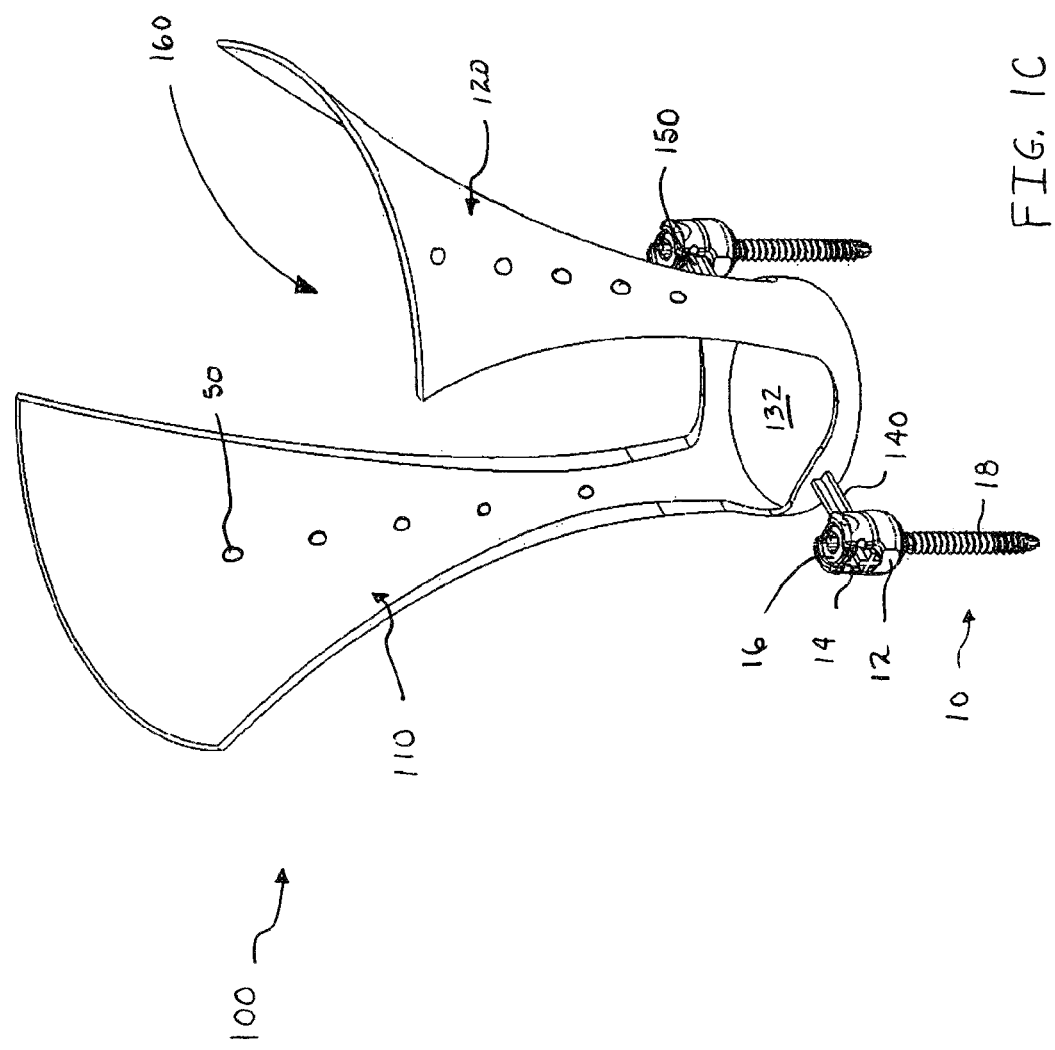

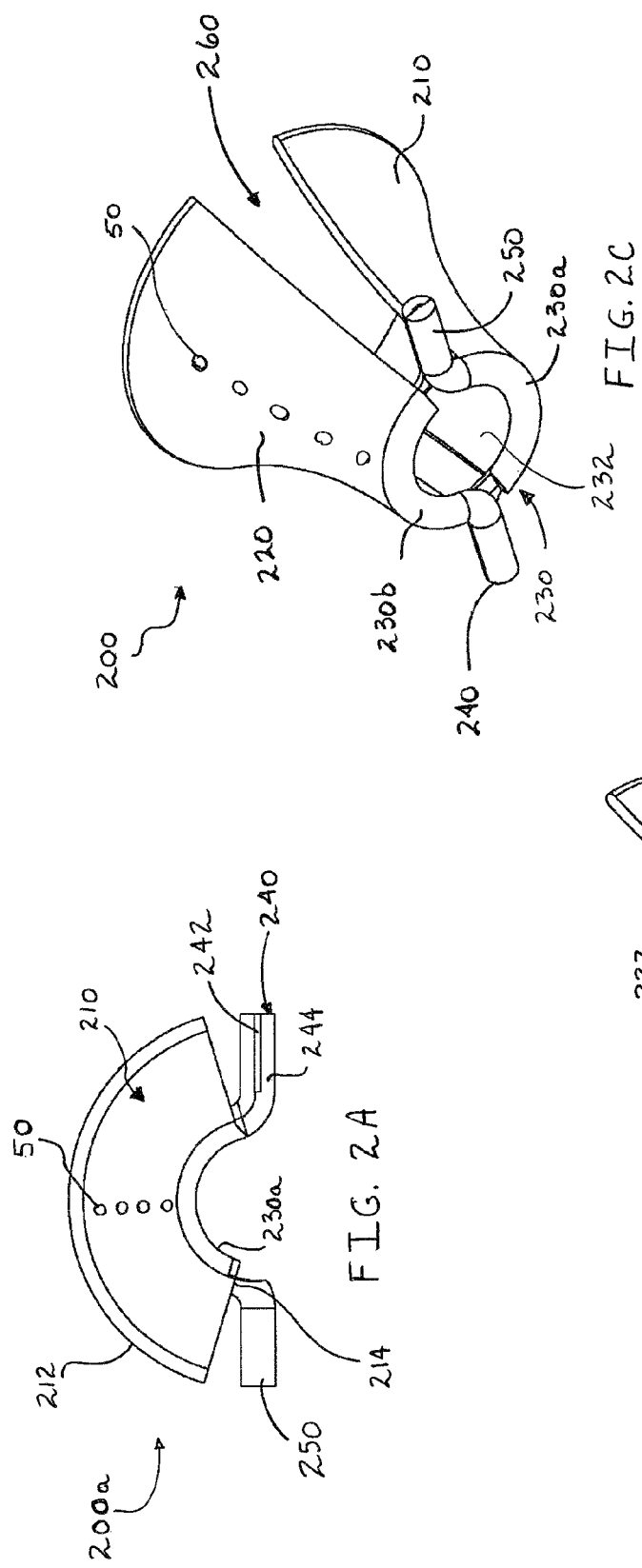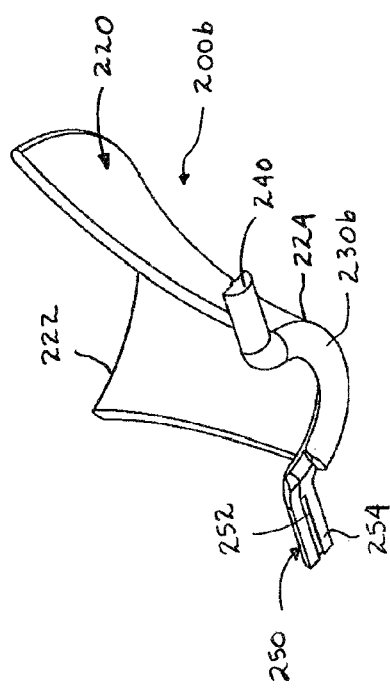

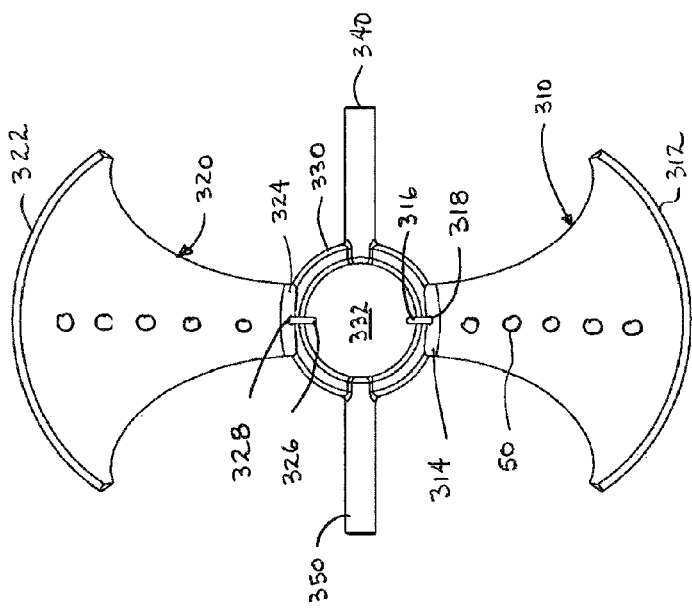
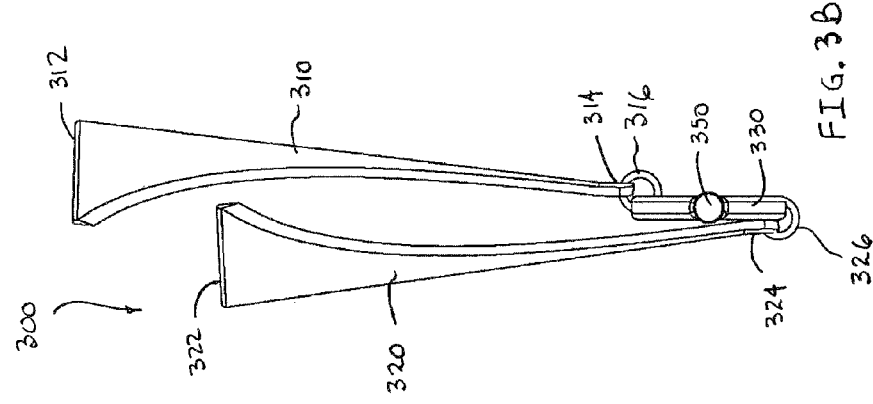
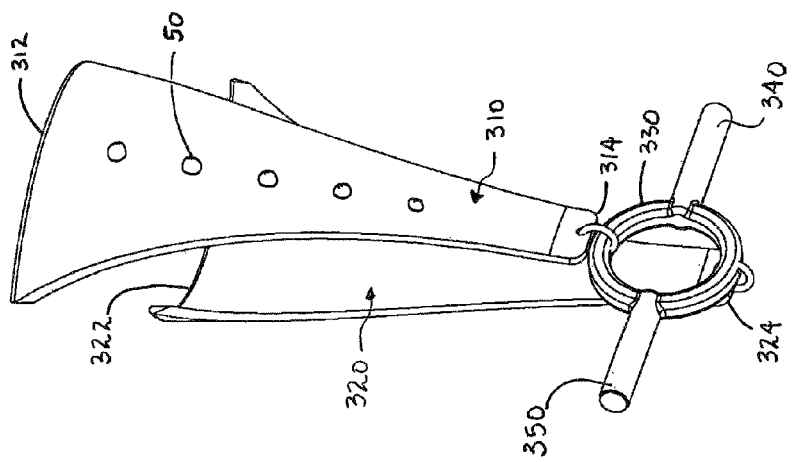

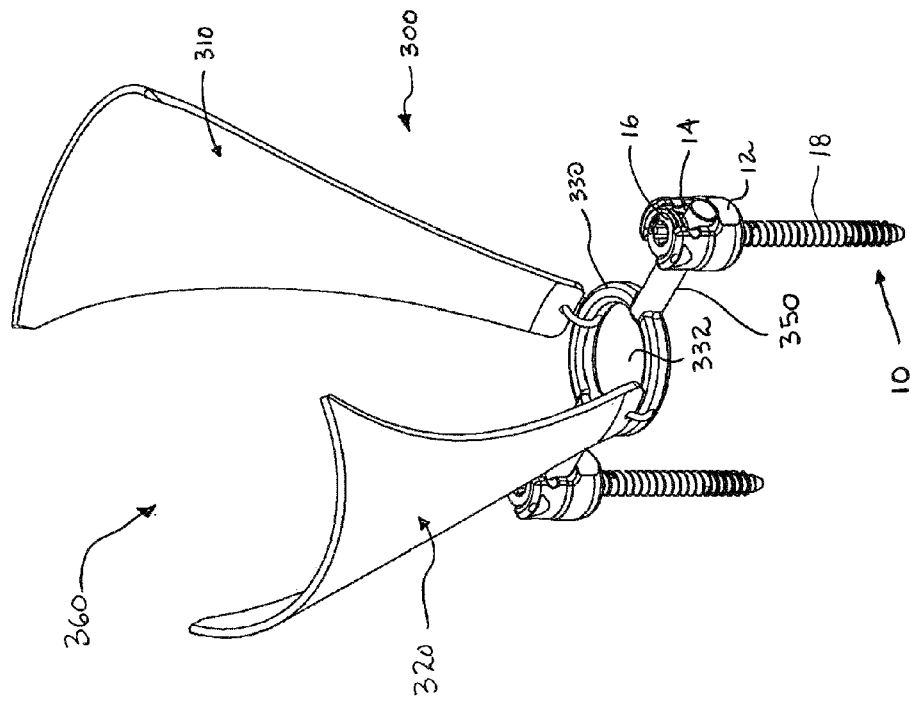
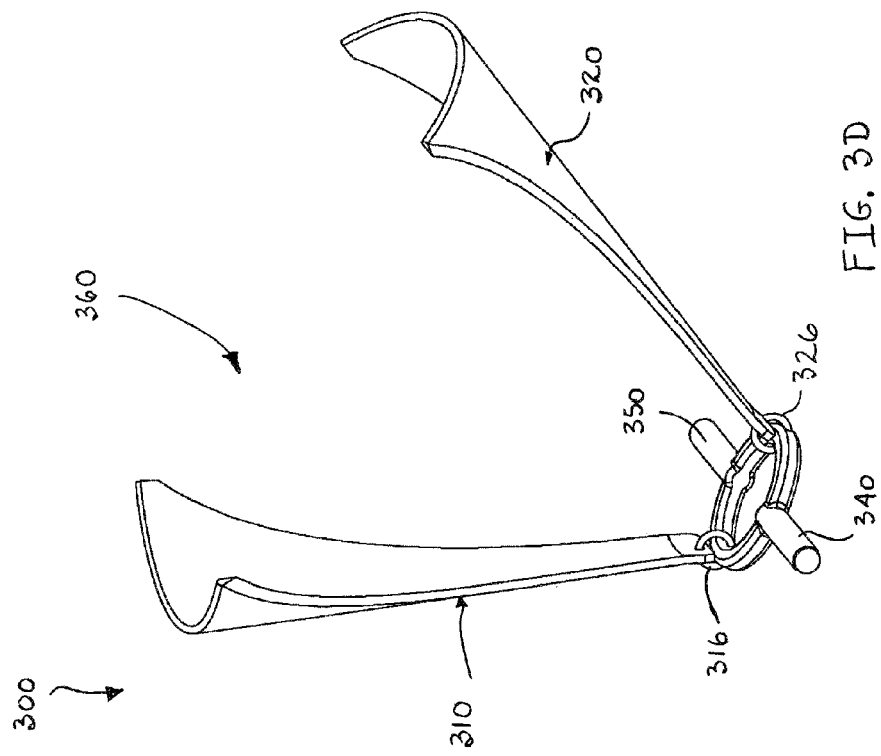

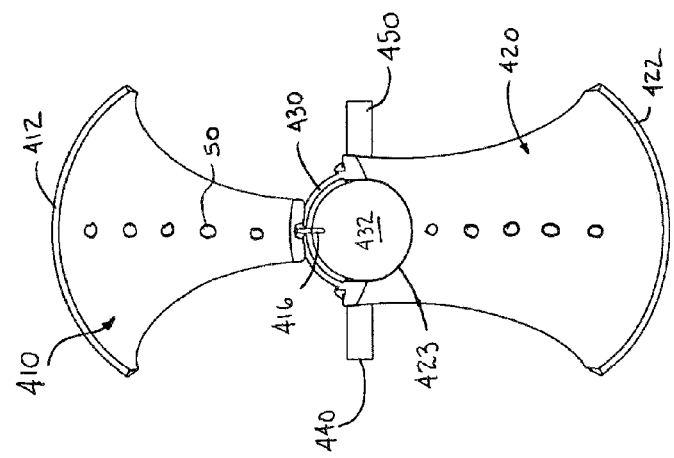
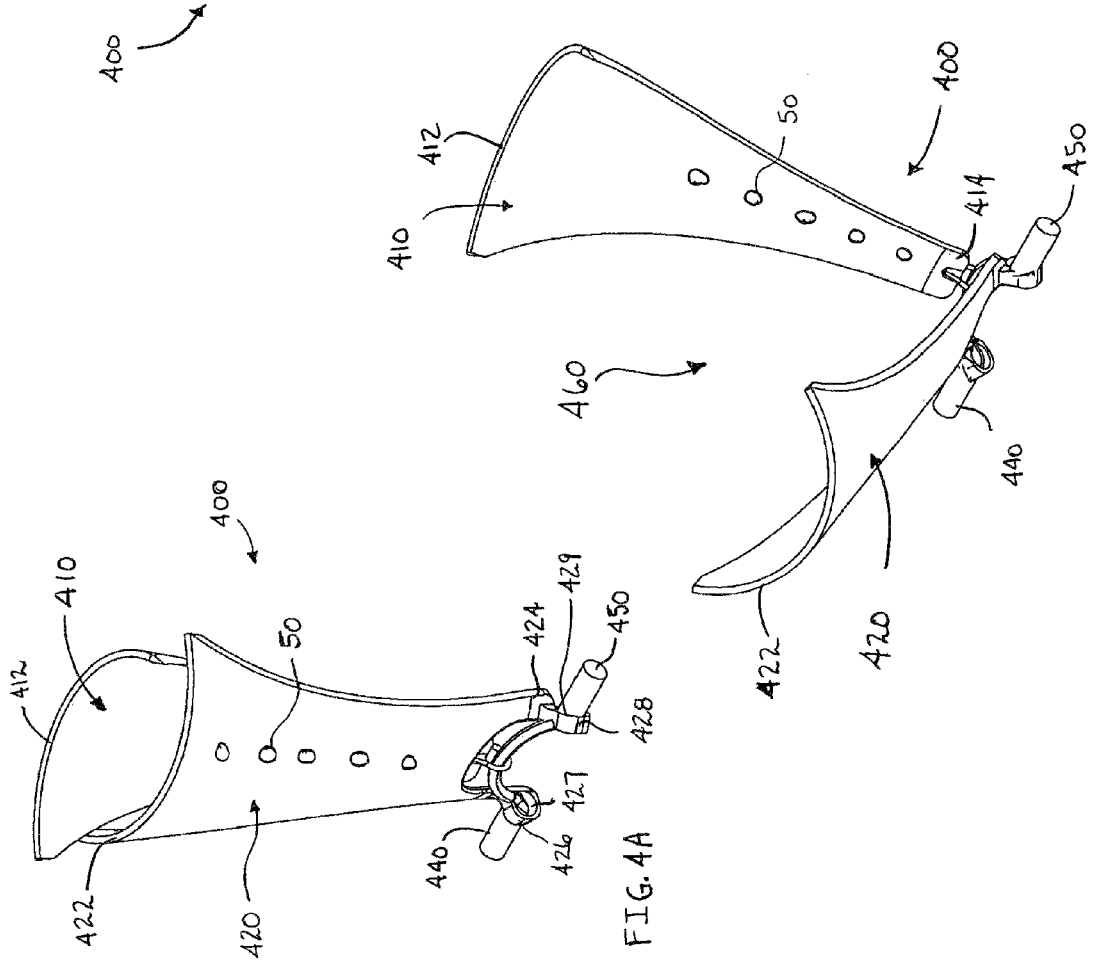
FIG. 4C
FIG. 4B
FIG. 4A

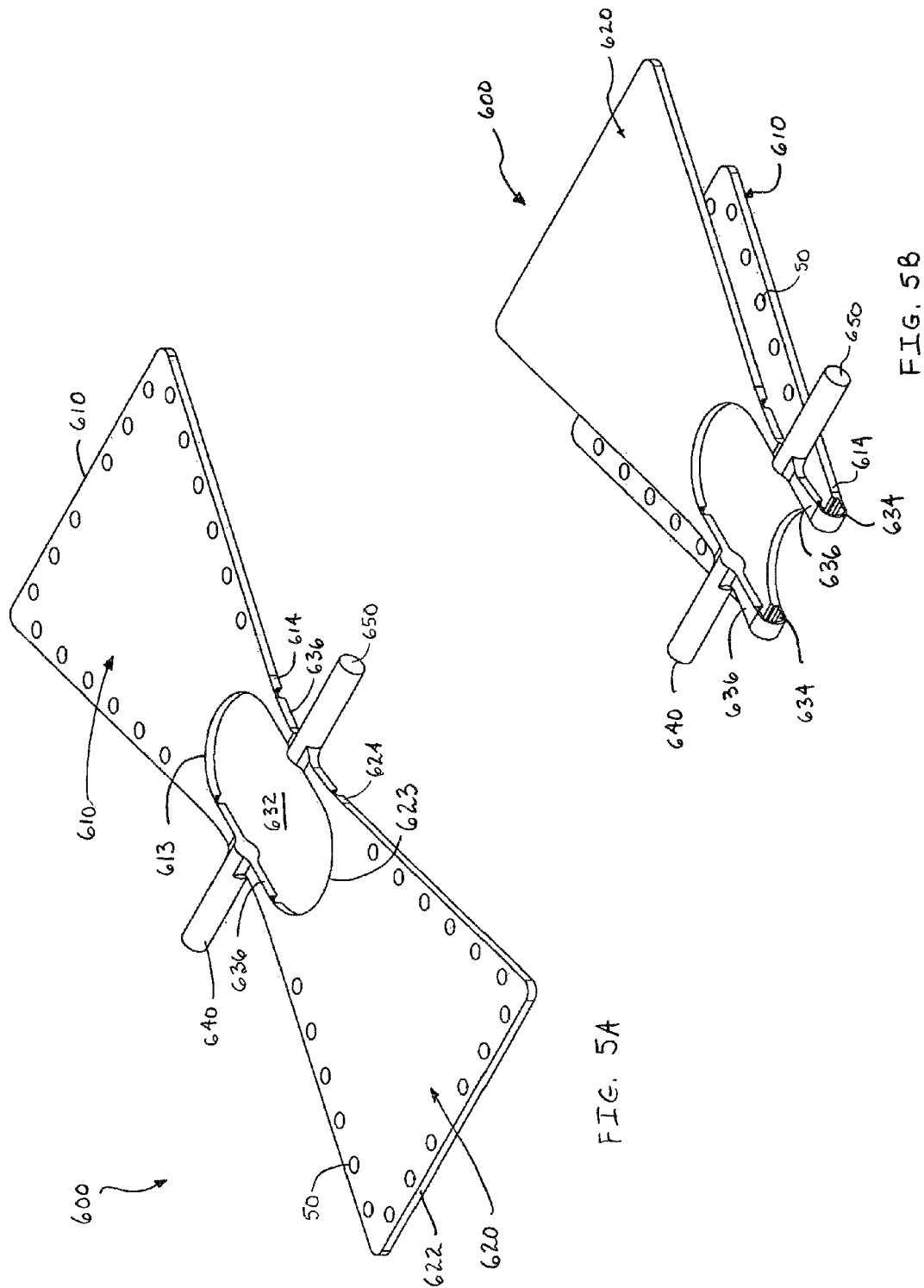

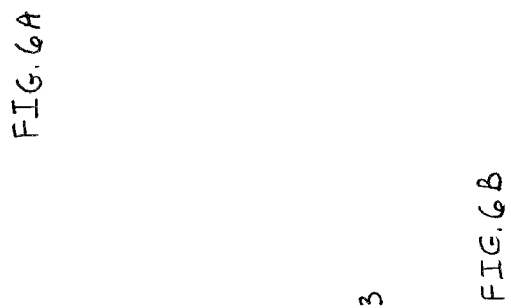
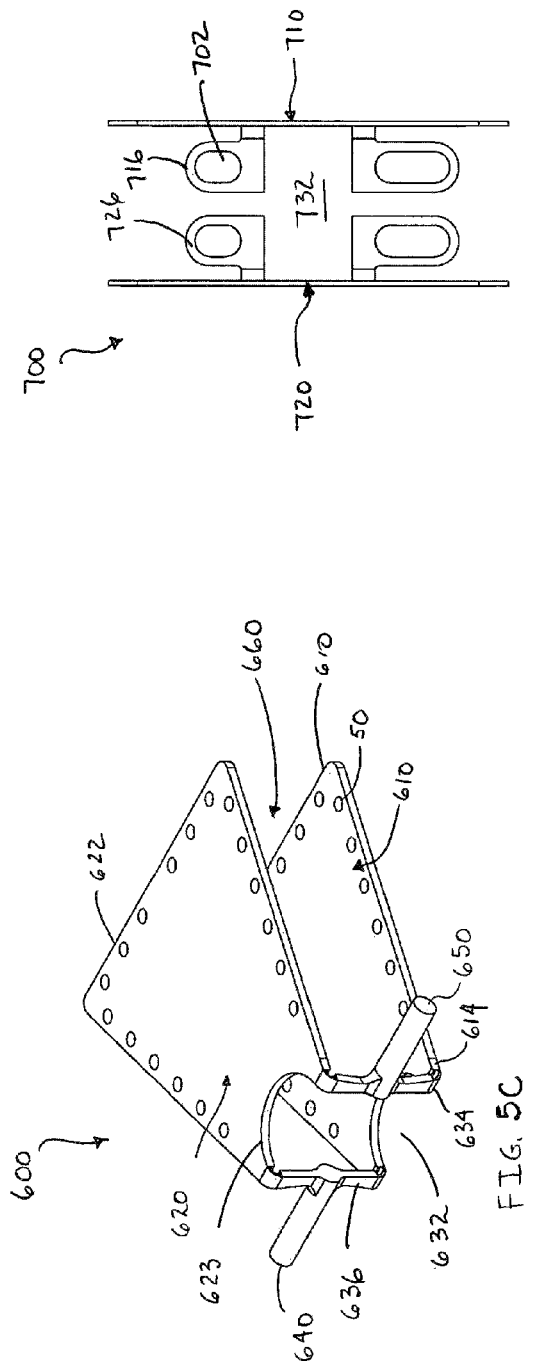
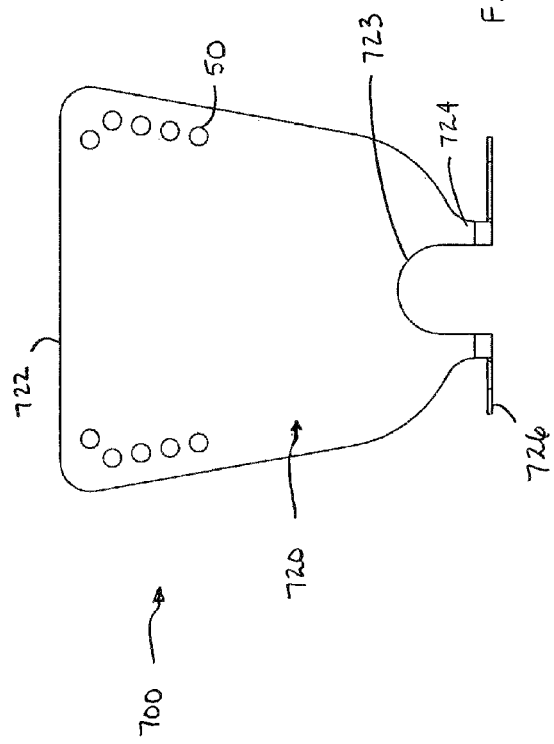

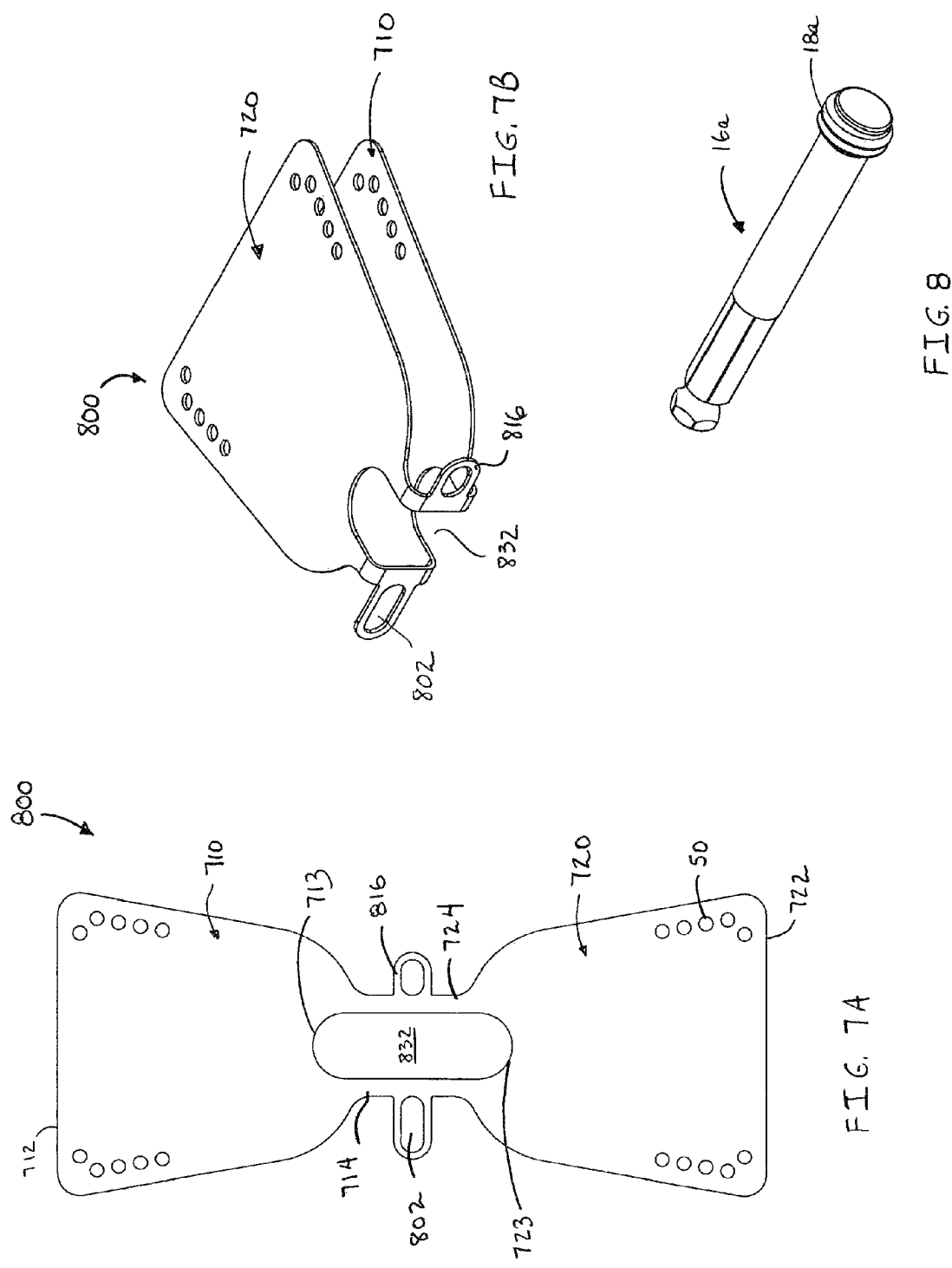

MINIMALLY OPEN RETRACTION DEVICE

CROSS-REFERENCE TO RELATED APPLICATIONS

This application is a divisional of U.S. patent application Ser. No. 14/228,639, filed on Mar. 28, 2014, which is a divisional of U.S. patent application Ser. No. 11/799,576, filed on May 2, 2007, now U.S. Pat. No. 8,696,560, which claims priority to, and the benefit of, U.S. Provisional Patent Application Ser. No. 60/796,921 filed on May 2, 2006, the entire contents of each of these prior applications are incorporated herein by reference.

BACKGROUND

1. Technical Field

The present disclosure relates generally to orthopedic spine surgery and, in particular, to a minimally open retraction device and methods for its use in a minimally open surgical procedure.

2. Background of Related Art

In recent years minimally open surgical approaches have been applied to orthopedic spine surgery and more recently to spine fusions involving one or more vertebral bodies. Unlike minimally invasive procedures such as arthroscopic knee surgery or gallbladder surgery where the affected area is contained within a small region of the body, spine surgery involving a fusion typically spans a considerably larger length or portion of the body. For this reason, the idea of performing a minimally open procedure on the spine has only recently been approached.

Minimally open surgery offers significant advantages over conventional open surgery. At the onset, the skin incision and subsequent scar are significantly smaller. By using more than one small incision rather than one large incision the need for extensive tissue and muscle retraction is greatly reduced. This leads to significantly less post-operative pain, shorter hospital length-of-stay and a faster recovery overall.

A truly minimally open spine procedure should constitute the smallest damage or disruption possible to the surrounding anatomy. While there may be more than one incision or one long incision, depending on the number of levels needing attention, it is the amount of muscle refraction and scraping that will result in less operative trauma for the patient. A minimally open procedure is also less expensive, reduces hospitalization time, causes less pain and scarring, reduces the incidence of complications, such as surgical site infections, and has an increased speed of recovery.

A typical spine fusion in the lumbar region, whereby at least two vertebral bodies are rigidly connected using screws implanted into the vertebral body and a solid metal rod spanning the distance between said screws, is by its nature not very conducive to a minimally open approach. Furthermore, a spine fusion is typically supported by implanting one or more interbodies into the disc space either using an anterior or posterior approach. An anterior approach requires a separate incision whereby the surgeon accesses the patient's spine through the abdomen. One advantage is the interbody used in this procedure closely matches the footprint of the adjacent vertebral bodies. The disadvantage is that an anterior procedure is typically performed at a different time and requires its own incision and access.

A posterior approach to interbody implantation can be achieved through the same incision as that of the pedicle screws. Implantation of a Posterior Lumbar Interbody Fusion (PLIF) device requires bilateral removal of the facet joint while implantation of a Transforaminal Lumbar Interbody Fusion (TLIF) device can be achieved unilaterally and may require removal of only one facet joint. The advantage of the TLIF is that only one device is implanted into the disc space whereas a PLIF requires two bilateral implants.

While the implantation of pedicle screws can be achieved with relatively little site preparation, interbody implantation requires considerable work. Once the facet joint is removed, the surgeon can begin removing the disc. One or more instruments may be needed to access the site at any time as well as sufficient lighting and suction. To perform these tasks the surgeon needs a suitable opening or channel to work through.

There has been considerable development of retractors and retractor systems for minimally invasive procedures, with most of the new technologies being based on traditional types of surgical retractors for open procedures, predominantly table-mounted devices of various designs. These prior art devices are large and bulky and frequently do not adapt well to a less invasive approach. Standard hand-held surgical retractors are well known in the prior art and can be modified to fit the contours of these smaller incisions, but they require manual manipulation to maintain their position. Typical retractors also are positioned into the soft tissue and levered back to hold the wound open, frequently requiring re-positioning if they dislodge, obstruct the view, or the access ways.

Several minimally open or minimally invasive access devices currently exist to achieve the goal of a suitable working channel. Most are either mounted to the surgical table or held in place by the surgeon or an assistant. Table mounted retractors offer little by way of flexibility. Furthermore, they do not offer a relationship or positional guidance with respect to the patient.

Handheld retractors offer greater flexibility but require an extra hand to maintain position. They also may or may not offer a fixed relationship to the patient but in either case can easily be knocked out of position. Furthermore, handheld retractors typically offer a very long and narrow fixed channel to work through making the procedure even more challenging. Finally, any of the above mentioned retractors typically require a form of dilation to obtain the initial opening. Circular or oblong dilators are well known in the art.

SUMMARY

The present disclosure is directed towards retractors configured for use in minimally invasive procedures. In particular, embodiments of the present disclosure include retractors that are configurable for insertion through a minimal opening in the patient's skin and are reconfigurable for retracting tissue surrounding a selected operative site.

According to one embodiment of the present disclosure, the minimally open retraction device includes first and second elongate members or blades. The blades are generally arcuate and define a generally funnel shaped channel that extends through the retractor. A ring member is attached to the distal ends of the blades. The ring member has an opening extending therethrough. The blades are repositionable between a closely approximated position and a spaced apart position. In the closely approximated position, the retractor is insertable and removable through the incision in the patient's skin. After the retractor is inserted into an operative site, the blades are manipulated by the practitioner to retract tissue surrounding the operative site. In addition, the ring member may include opposing rod portions for attaching the retractor to pedicle screws located in the operative site.

According to another presently disclosed embodiment, the retractor includes first and second sections. Each section includes a ring portion attached to a distal end of an elongate member or blade. The blade has a generally arcuate configuration. A pair of rod portions extends outwards from opposing ends of the ring portion. The rod portions of one section include complementary structures for slidably engaging the corresponding rod portions of the other section such that the rod portions are slidable relative to each other. When assembled, the ring portions define an opening and the arcuate blades define a generally funnel shaped channel that is in communication with the opening. Since the rod portions are slidably coupled, the size and shape of the opening is variable. As in the previous embodiment, the retractor may be coupled to pedicle screws.

In a further embodiment of the minimally open retraction device or retractor, the retractor includes a pair of elongate members or blades that are operatively coupled to a ring member. The ring member is located at the distal ends of the blades and has an opening therethrough. Each blade includes a hole near its distal end. The hole cooperates with a loop that is attached to the ring member such that each blade is pivotally coupled to the ring member. A pair of opposing rod portions is attached to the ring member. As such, the retractor blades can be repositioned into close approximation with each other that rotates the ring about an axis of the rod portions. In this state, the retractor has a minimal profile and may be inserted through a minimal incision or opening in the patient. Once inserted, the retractor is manipulated to a second state for retracting tissue surrounding the operative site. As in previous embodiments, the retractor may be attached to pedicle screws located in the operative site.

In an alternative embodiment of the present disclosure, the minimally open retraction device or retractor includes an arcuate member having opposing rod portions extending from the ends of the arcuate member. One blade includes a hole that cooperates with a loop attached to the arcuate member. The other blade has an arcuately shaped cutout in its distal region and a pair of protrusions with bores. The bores are sized to cooperate with the rod portions such that the blade is rotatable about the rod portions. In addition, the arcuate cutout and the arcuate member define an opening in the retractor.

BRIEF DESCRIPTION OF DRAWINGS

Embodiments of the presently disclosed minimally open retraction device are described herein with reference to the accompanying drawings, wherein:

FIG. 1A is a top view of a minimally open retraction device according to an embodiment of the present disclosure;

FIG. 1B is a front perspective view of the minimally open retraction device of FIG. 1A;

FIG. 1C is a front perspective view of the minimally open retraction device of FIG. 1A attached to a pair of pedicle screws;

FIG. 2A is a top view of a first section of a minimally open retraction device according to another embodiment of the present disclosure;

FIG. 2B is an enlarged bottom perspective view of a second section of the minimally open retraction device illustrating features of extension members;

FIG. 2C is a bottom perspective view of the two sections of the minimally open retraction device of FIGS. 2A and 2B as assembled;

FIG. 3A is a side perspective view of a minimally open retraction device according to a further embodiment of the present disclosure in a first state;

FIG. 3B is a front view of the minimally open retraction device of FIG. 3A;

FIG. 3C is a top view of the minimally open retraction device of FIG. 3A shown in a second state;

FIG. 3D is a front perspective view of the minimally open retraction device of FIG. 3C;

FIG. 3E is a side perspective view of the minimally open retraction device of FIG. 3A attached to a pair of pedicle screws;

FIG. 4A is a side perspective view of a minimally open retraction device in a first state according to an alternate embodiment of present disclosure;

FIG. 4B is a side perspective view of the minimally open retraction device of FIG. 4A in a second state;

FIG. 4C is a top view of the minimally open retraction device of FIG. 4A;

FIG. 5A is a perspective view of a further embodiment of the presently disclosed minimally open retraction device;

FIG. 5B is a bottom perspective view of the minimally open retraction device of FIG. 5A shown in one configuration;

FIG. 5C is a bottom perspective view of the minimally open retraction device of FIG. 5A shown in a second configuration;

FIG. 6A is a top plan view of a minimally open retraction device according to a further embodiment of the present disclosure;

FIG. 6B is a side plan view of the minimally open retraction device of FIG. 6A;

FIG. 7A is a top perspective view of a minimally open retraction device according to an alternate embodiment of the present disclosure;

FIG. 7B is a bottom perspective view of the minimally open retraction device of FIG. 7A in an insertion condition;

FIG. 8 is a side perspective view of a temporary set screw; and

DETAILED DESCRIPTION OF THE EMBODIMENTS

Figure 4E:
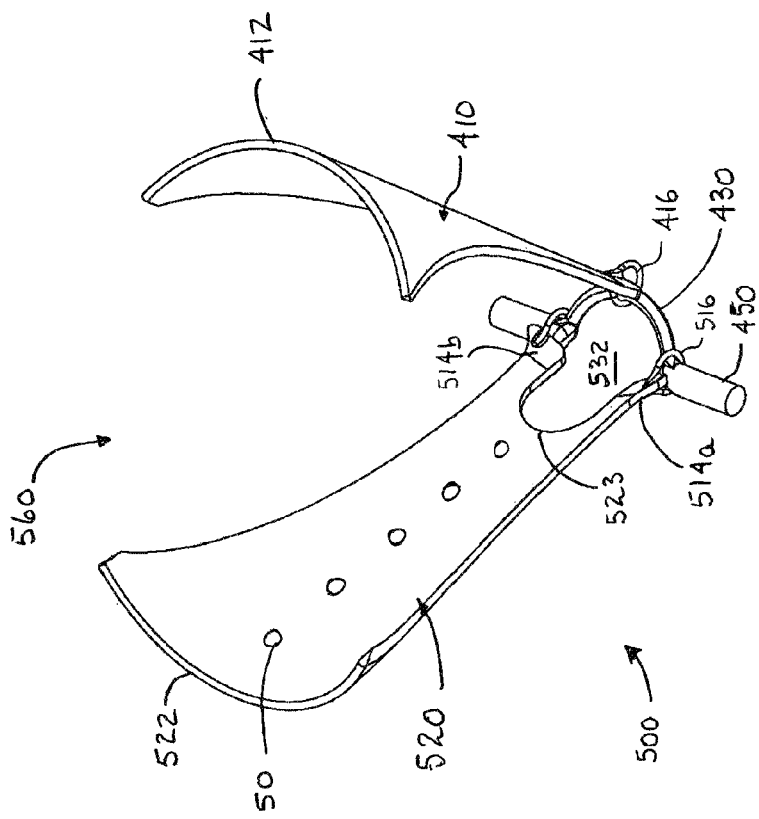
FIG. 4E is a top perspective view of an alternate embodiment of the minimally open retraction device of FIG. 4A.

Embodiments of the presently disclosed minimally open retraction device will now be described in detail with reference to the drawing figures wherein like reference numerals identify similar or identical elements. In the drawings and in the description which follows, the term "proximal", as is traditional, will refer to the end of the minimally open retraction device which is closest to the operator while the term "distal" will refer to the end of the device which is furthest from the operator.

Referring now in detail to FIGS. 1A-1C, in which like reference numerals identify similar or identical elements, a minimally open retraction device, in accordance with a first embodiment of the disclosure, is generally designated as 100.

As shown in FIGS. 1A and 1B, a minimally open retraction device, or retractor 100 includes first and second elongate members or blades 110, 120. Each of the blades 110, 120 include a proximal end 112, 122 and a distal end 114, 124. In addition, each blade 110, 120 is arcuately shaped and formed from a resilient polymeric material. The distal ends 114, 124 are attached to a ring 130 that includes an opening 132 therethrough. On opposing portions of the ring 130 are rod portions or extension members 140, 150. The ring 130 and the rod portions 140, 150 are formed from polyethylene. Although the rod portions 140, 150 are illustrated as having a cross shaped configuration, other geometric shapes are contemplated (e.g. circular, hexagonal, or rectangular). It is contemplated that the distal ends 114, 124 of the blades 110, 120 are integrally formed with the ring 130.

It is further contemplated that other suitable biocompatible materials (e.g. polyethylene, polypropylene, polycarbonate, polyetheretherketone, stainless steel, or titanium) may be used. In instances where a metallic material is selected, the material has a thickness that allows each blade 110, 120 to bend and retract tissue. It is also contemplated that the thickness of each blade 110, 120 may vary along its length, thereby adjusting its rigidity and flexibility for a selected procedure.

The ring member 130 is formed from a material that is more rigid than the material selected to form blades 110, 120. By forming the ring member 130 from a more rigid material than the blades 110, 120, the geometry of the retractor 100 and the opening 132 are maintained during retraction of the surrounding tissue. In addition, each of the blades 110, 120 include a plurality of orifices 50. The orifices 50 are adapted to cooperate with a conventional instrument such as a Gelpi retractor.

Each blade 110, 120 is generally arcuate such that when the blades 110, 120 are moved towards each other (i.e. approximated), the retractor 100 defines a funnel shaped channel 160 therebetween. The channel 160 is in communication with the opening 132 of the ring 130. As such, the channel 160 permits access to the operative site and the introduction and/or removal of surgical instruments, tissue, or prosthetic devices from the operative site.

In addition, as shown in FIG. 1C, the retractor 100 may be coupled to a pair of pedicle screws 10. As is known in the art, the pedicle screws may be monoaxial or polyaxial. Each pedicle screw 10 includes a head 12 defining a channel 14. A set screw 16 may be threaded into the head 12. The pedicle screw 10 also includes a threaded shank 18 for engagement with a selected bone structure (e.g. a vertebral body). Each of the rod portions 140, 150 is configured and adapted to fit within the channel 14 of the pedicle screw 10. When a rod portion 140, 150 is positioned within the channel 14, the set screw 16 is tightened and secures the rod portion 140, 150 relative to the pedicle screw 10. The set screw 16 may be loosened so that the practitioner may adjust the positioning of the rod portion 140, 150 relative to the pedicle screw 10 and then re-tightened when the rod portion 140, 150 is in a desired position. In addition, the structural rigidity of the ring member 130 maintains the distance between the pedicle screws 10 during the surgical procedure.

The retractor 100 is installed through an incision or opening created in the patient's skin using techniques and instruments that are known in the art. In one embodiment, the retractor 100 is installed through a minimal incision or opening. Once the incision is made in a desired location and the pedicle screws 10 are positioned in the selected bone structures, the retractor 100 is inserted into the incision. Working subcutaneously, the practitioner manipulates the retractor 100 into a desired position and maneuvers the rod portions 140, 150 into the channels 14 of the respective pedicle screws 10. The retractor 100 may then be moved along an axis defined between the pedicle screws 10, thereby allowing the practitioner to finely adjust the location of the retractor 100. Once the retractor 100 is in the desired location, the practitioner tightens the set screws 16 to secure the position of the retractor 100. Additionally, one or both of the set screws 16 may be loosened or loosely installed in their respective pedicle screws 10, thereby allowing the practitioner to reposition the retractor without necessitating removal and reinstallation of the retractor 100. Subsequent to any repositioning, the practitioner tightens the set screws 16 to lock the retractor 100 in position.

Once the retractor 100 is in the desired location, the practitioner manipulates the blades 110, 120 by bending them outwards to retract tissue at the operative site, thereby increasing the size of the access opening at the operative site. As such, the retractor 100 may be inserted through a relatively small opening and expanded to enlarge the opening for subsequent surgical procedures. Instruments, tissue, and/or prosthetic devices may then be inserted or removed through the opening 132. The channel 160 and the opening 132 provide a convenient access portal for the practitioner to perform surgical procedures at the operative site.

Advantageously, the shape of the access opening created using the devices and methods disclosed herein is generally funnel shaped, with a narrower section disposed within the incision localized on the area of interest between the pedicle screws, the location of the ring at the base of the funnel being secured relative to the pedicle screws. The funnel shape defined by the retractor with the flexible blades spread apart provides increased access space at the proximal portion of the incision, thereby providing increased visibility and the ability to insert and remove additional instrumentation such as suction, irrigation or lighting without interfering with the surgeon's ability to operate in the operative area at or below the bottom of the funnel shaped device.

In an alternate embodiment of the present disclosure, a minimally open retraction device is illustrated in FIGS. 2A-2C. The minimally open retraction device, or retractor is generally designated as 200 (FIG. 2C). FIG. 2A illustrates one section 200a of the retractor 200 with the other section 200b being substantially similar. The section 200a includes an elongate member or blade 210 having a proximal end 212 and a distal end 214. The blade 210 is arcuately shaped and formed from a flexible polymeric material similar to the materials used in manufacturing retractor 100. An arcuate ring 230 is attached to the distal end of the retractor 200. The arcuate ring 230 is formed from ring portions 230a, 230b that are at the distal ends 214, 224 of the blades 210, 220 (FIG. 2C). It is contemplated that the distal ends 214, 224 are integrally formed with the ring portions 230a, 230b. At the ends of the ring member 230, a pair of opposing rod portions 240, 250 is attached. The ring member 230 and the rod portions 240, 250 combine to define a substantially hemispherical structure. In particular, the rod portions 240, 250 are attached to opposing ends of the ring member 230 and extend outwards therefrom. The ring member 230 is formed from a resilient polymeric material and may be stretched or compressed accordingly.

The rod portions 240, 250 are generally hemispherical structures. Each of the rod portions 240, 250 include a planar surface 244, 254. As shown in FIGS. 2B and 2C, the planar surface 244 of rod portion 240 is separated from the planar surface 254 of rod portion 250 by approximately 180°. Further still, the planar surface 244 includes a rib 242 that extends above the surface of planar surface 244. The planar surface 254 includes a channel 252 that is recessed below the planar surface 254. The rib 242 and the channel 252 are complementary in that they are both configured and dimensioned for slidably engaging one another.

As assembled, the retractor 200 (FIG. 2C) includes first and second sections 200a, 200b. The sections 200a, 200b are coupled together such that the ribs 242 slidably engage the channels 252 as described hereinabove. This arrangement permits the practitioner to vary the size of the opening 232 as will be described in detail hereinbelow. As in the previous embodiment, the blades 210, 220 are bendable in relation to the ring 230 such that the retractor 200 retracts tissue surrounding the operative site.

Similar to the previous embodiment, the operative site is prepared by forming an incision or an opening in the patient's skin using known techniques and equipment. The pedicle screws 10 may be installed in the selected bone structures either before the incision is made or subsequent to its creation. Once the incision is created at the operative site, the practitioner installs the retractor 200.

In a first technique, the practitioner couples the first and second sections 200a, 200b as described above and inserts the assembled retractor 200 into the incision. The assembled retractor 200 may be positioned between the pedicle screws 10 using the techniques discussed with regards to retractor 100. As such, the retractor 200 may be substituted for the retractor 100 that is illustrated in FIG. 1C. The slidable arrangement between the first and second sections 200a, 200b permits the practitioner to vary the size and configuration of the opening 232. After the assembled rod portions 240, 250 are positioned in their respective channels 14 of the pedicle screws 10, the practitioner may slide the respective rod portions 240, 250 relative to one another, thereby expanding or contracting (i.e. re-configuring) the opening 232. Thus, the retractor 200 is capable of being installed through an incision and joining adjacent pedicle screws 10 without the necessity of sizing the retractor 200 to the operative site prior to commencing the surgical procedure. As such, the increased flexibility of the retractor 200 allows the practitioner to install the pedicle screws 10 in desired locations, form the incision between the pedicle screws 10, install the retractor 200, and adjust the size of the opening 232 for accommodating the distance between the pedicle screws 10.

As shown in FIG. 2C, the retractor 200 is in its default condition. In this condition, the effective length of the retractor 200 is defined by the distance between the distal ends of the rod portions 240, 250 of either section 200a, 200b. If the distance between the pedicle screws 10 is greater than the distance between the end regions of the rod portions 240, 250, the practitioner merely slides the rod portions 240, 250 away from each other (i.e. away from a center of the opening 232) and effectively increases the overall length of the retractor 200 such that it may be attached to the pedicle screws 10 and locked in position using the set screws 16. Alternatively, if the distance between the pedicle screws 10 is less than the distance between the rod portions 240, 250, the practitioner may slide the rod portions 240, 250 towards each other (i.e. towards a center of the opening 232) and effectively reduce the overall length of the retractor 200 prior to securing it to the pedicle screws 10 using the set screws 16. In addition, by altering the effective length of the retractor 200, the configuration of the opening 232 in ring 230 is also altered. When the effective length of the retractor 200 is increased, the ring portions 230a, 230b are stretched and define a generally elliptical opening having its long axis along a longitudinal axis of the rod portions 240, 250. When the effective length of the retractor 200 is decreased, the ring portions 230a, 230b are compressed forming a generally elliptical opening with its short axis along the longitudinal axis of the rod portions 240, 250.

Referring now to FIGS. 3A-3E, a further embodiment of the present disclosure is illustrated. The minimally open retraction device or retractor is generally designated as 300. The retractor 300 includes first and second elongate members or blades 310, 320. Each blade 310, 320 includes a proximal end 312, 322 and a distal end 314, 324. In addition, each blade 310, 320 has a generally arcuate shape. The ring member 330 is attached to the distal ends 314, 324 of the blades 310, 320. The ring member 330 is a circular structure having an opening 332 and a pair of outwardly extending rod portions 340, 350. As in each of the previous embodiments, the ring member is formed from a material having greater rigidity (i.e. structural strength) that the material used to form each of the blades 310, 320. By using a more rigid material, the ring member 330 maintains its geometry during the surgical procedure and further maintains the distance between the pedicle screws 10 as will be discussed hereinbelow in connection with FIG. 3E.

Each of the rod portions 340, 350 have a generally cylindrical shape and are located in opposition to one another such that they are approximately 180° apart from each other on an outer surface of the ring member 330. The rod portions 340, 350 may also have different geometric configurations such as rectangular, hexagonal, or cross shaped. The blades 310, 320 are pivotally coupled to the ring member 330 and are positioned such that the points of attachment are approximately 180° apart on the ring member 330. In one embodiment, the distal ends 314, 324 are pivotally coupled to the ring member 330 via loops 316, 326. The loops 316, 326 are fixedly attached to the ring member 330, while each of the blades 310, 320 are movable along the loops 316, 326 via a hole 318, 328 (FIG. 3E) in each of the blades 310, 320. Thus, the blades 310, 320 are capable of retracting surrounding tissue once the retractor 300 is positioned in a desired location by urging the blades 310, 320 away from each other and retracting the surrounding tissue. As in the previous embodiments, one or both of the blades 310, 320 may be manipulated to retract tissue.

The retractor 300 is capable of being transitioned from a first condition (FIG. 3A) to a second condition (FIG. 3C). In the first condition, the retractor 300 has a minimum profile, thereby facilitating its insertion into an operative site since the blades 310, 320 are in close approximation with each other and the ring member 330 is substantially parallel with at least one of the blades. By manipulating the blades 310, 320, the practitioner rotates the ring member 330 to a position that is substantially perpendicular to the blades 310, 320 (i.e. the second condition) when the retractor 300 is located in the operative site, thereby defining the opening at the base of the retractor 300 adjacent the pedicle screws 10.

Specifically referring to FIG. 3E, the retractor 300 is shown connected to a pair of pedicle screws 10. The pedicle screws 10 are attached to selected bone structures in the patient's body using techniques and instruments that are known in the art. Once the incision is made in a desired location and the pedicle screws 10 are positioned in the selected bone structures, the retractor 300 is inserted into the incision with the retractor 300 initially in its first condition (i.e. a minimal profile). Working subcutaneously, the practitioner manipulates the retractor 300 into a desired position and maneuvers the rod portions 340, 350 into the channels 14 of the respective pedicle screws 10. The retractor 300 may then be moved along an axis defined between the pedicle screws 10 allowing the practitioner to finely adjust the location of the retractor 300. Once the retractor 300 is in the desired location, the practitioner tightens the set screws 16 to secure the position of the retractor 300. Alternatively, one or both of the set screws 16 may be loosened or loosely installed in their respective pedicle screws 10, thereby allowing the practitioner to reposition the retractor without necessitating removal and reinstallation of the retractor 300. Subsequent to any repositioning, the practitioner tightens the set screws 16 to lock the retractor 300 in position.

Once the retractor 300 is in the desired location, the practitioner manipulates the retractor 300 and spreads apart the retractor blades 310, 320, such that the retractor 300 transitions from its first condition to its second, funnel-shaped condition, thereby allowing the practitioner access to the operative site and retracting tissue surrounding the operative site. In addition, the practitioner manipulates the blades 310, 320 by bending them outwards to retract tissue at the operative site, thereby increasing the size of the opening at the operative site. As such, the retractor 300 may be inserted through a relatively small opening and expanded to enlarge the opening for subsequent surgical procedures. Instruments, tissue, and/or prosthetic devices may then be inserted or removed through the opening 332. The channel 360 and the opening 332 provide a convenient access portal for the practitioner to perform surgical procedures at the operative site. In addition, since the ring member 330 is formed from a material that is more rigid than the material selected for the blades 310, 320, the ring member 330 maintains its geometric configuration during the retraction process. Additionally, since the ring member 330 resists deformation, it maintains the relative positions of the pedicle screws 10 to each other during the retraction procedure.

Another embodiment of the presently disclosed minimally open retraction device is illustrated in FIGS. 4A-4D and is generally designated as 400. The minimally open retraction device or retractor 400 includes first and second elongate members or blades 410, 420. Each blade 410, 420 includes a proximal end 412, 422 and a distal end 414, 424. In addition, each blade 410, 420 has a generally arcuate shape. The distal end 424 of the blade 420 has an arcuately shaped cutout 423. An arcuate member 430 is releasably and pivotably coupled to the distal ends 414, 424 of the blades 410, 420. The arcuate member 430 has a pair of outwardly extending rod portions 440, 450. Each of the rod portions 440, 450 has a generally cylindrical shape and is located in opposition to one another such that they are approximately 180° apart from each other on an outer surface of the arcuate member 430. In particular, the rod portions 440, 450 extend in opposing directions from ends of the arcuate member 430.

In this embodiment, one blade 410 is pivotally coupled to the ring member 430 via a loop 416. The loop 416 is slidably attached to the ring member 430 and the blade 410 is movable along the arcuate member 430 by sliding the blade 410 and the loop 416. Thus, the blade 410 is capable of retracting surrounding tissue once the retractor 400 is positioned in a desired location by urging the blade 410 away from the opposing blade 420 and retracting the surrounding tissue. In addition, the blade 410 may be repositioned relative to the rod portions 440, 450 by sliding the blade 410 and the loop 416 along the arcuate path defined by the ring member 430. The other blade 420 has first and second protrusions 426, 428 depending therefrom. Each of the protrusions 426, 428 has a bore 427, 429 extending therethrough. The bores 427, 429 are configured to cooperate with the rod portions 440, 450 such that the protrusions 426, 428 are rotatable about the rod portions 440, 450. Accordingly, the blade 420 is rotatable about the rod portions 440, 450. When the blade 420 is moved away from the blade 410, the cutout 423 and the arcuate member 430 define a circular opening 432 through the retractor 400. Additionally, the arcuately shaped blades 410, 420 define a funnel shaped channel 460 when they are spaced apart from one another (FIG. 4C) which is wider at the proximal portion of the incision and narrower adjacent the pedicle screws 10. As in the previous embodiments, one or both of the blades 410, 420 may be manipulated to retract tissue. In addition, the retractor 400 has at least a first condition and a second condition. In the first condition, the blades 410, 420 are in close approximation with each other and define a minimum profile (i.e. the first condition) for the retractor 400. In the first condition, the retractor 400 is adapted and configured for insertion into a relatively small opening or incision in the patient's skin. In the second condition, the retractor 400 is configured and adapted for retracting tissue surrounding the operative site. Once the retractor 400 is positioned in a selected location, the practitioner manipulates the blades 410, 420 away from each other and retracts the tissue surrounding the operative site. As the blade 420 is manipulated, the protrusions 426, 428 rotate relative to the rod portions 440, 450 thereby increasing the size of the opening 432. Retracting tissue using the retractor 400 is substantially similar to retracting tissue with previous embodiments of the retractor. In addition, the retractor 400 can be attached to a pair of pedicle screws in the same manner as the retractor 300 as illustrated in FIG. 4D. The arcuate member 430 is formed from a material that is more rigid than the material used to form the blades 410, 420 and has the attendant advantages discussed with respect to the ring member 330.

Figure 4D:
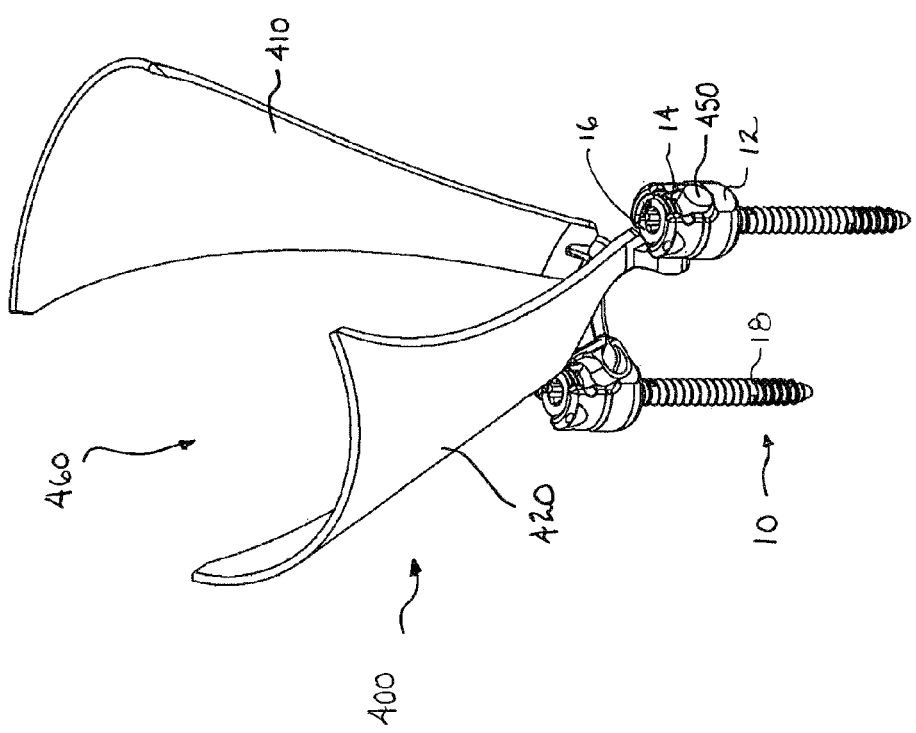
FIG. 4D is a side perspective view of the minimally open retraction device of FIG. 4B attached to a pair of pedicle screws.

A further embodiment of the retractor is illustrated in FIG. 4E and is generally designated as 500. The retractor 500 has substantially the same or similar components as the retractor 400 with the differences being discussed in detail hereinafter. In this embodiment, blade 520 has a proximal end 512, an arcuate cut-out 523, and a pair of distal end portions 514a, 514b. A loop 516 is attached to each distal end portion 514a, 51b. The loops are configured and adapted to encircle the rod portions 440, 450 such that the blade 520 is pivotable about the rod portions 440, 450. The arcuate cut-out 523 and the ring member 430 define an opening 532. The blades 410, 520 have a generally arcuate configuration and define a funnel shaped channel 560 therebetween when the instrument is in a second condition. As in the previous embodiments, the retractor 500 can be manipulated between a first condition having a minimal profile for insertion into a minimal incision in the patient's skin and a second condition for retracting tissue and accessing the operative site. In the second condition, instruments, prosthetics, and/or tissue may be inserted or removed through the channel 560, which provides access to the operative site for the practitioner. Additionally, the blades 410, 520 include a plurality of orifices 50.

Referring now to FIGS. 5A-5C, an alternate embodiment of the presently disclosed minimally invasive retraction device or retractor is illustrated and referenced as 600. In this embodiment, the retractor 600 is formed as an integrated unit similar to the retractor 100 (FIG. 1A). The retractor 600 includes elongate members or blades 610, 610 and rod portions 640, 650. Each of the blades 610, 620 include a plurality of orifices 50. Additionally, the blades 610, 620 include a proximal end 612, 622 and distal end portions 614, 624. The distal end portions 614 of the blade 610 are spaced apart from one another and define an arcuate cut-out 613. Similarly, the distal end portions 624 of the blade 620 are spaced apart from one another and define an arcuate cut-out 623. The arcuate cut-outs 613, 623 define an opening 632 through the retractor 600. Furthermore, each of the distal end portions 614, 624 includes a notch 634 that extends partially through the respective distal end portion 614, 624 and defines a flexion joint about which the blades 610, 620 may be bent that is best illustrated in FIGS. 5B and 5C. A strut 636 connects the distal end portions 614, 624 to the rod portions 640, 650.

The retractor 600 is initially substantially planar (FIG. 5A) and is manipulated by the practitioner such that the blades 610, 620 are moved towards each other with the notches 634 defining the point about which the blades 610, 620 bend. After the blades 610, 620 are bent (FIG. 5B), the retractor 600 is in a first condition and has a minimal profile, thereby allowing the retractor 600 to be inserted into a minimal opening in the patient's skin. Once the retractor is positioned in a selected area of the patient's body, the practitioner can manipulate the retractor 600 to place it in a second condition (FIG. 5C) for retracting tissue surrounding the selected operative site. In the second condition, the blades 610, 620 define a channel 660 therebetween. In particular, the channel 660 is in communication with the opening 632 and permits access to the operative site for the introduction and/or removal of surgical instruments, tissue, or prosthetic devices from the operative site.

The retractor 600 further includes rod portions 640, 650 for releasably coupling the retractor 600 to a pair of pedicle screws using the same techniques previously discussed with respect to the refractor 100.

The blades 610, 620 may be formed from suitable materials as previously discussed with regards to the blades 110, 120 of the retractor 100. The struts 636 are formed of a more rigid material than are the blades 610, 620. Using a more rigid material for the struts 636 provides the same benefits to the retractor 600 as did the ring member 330 to the retractor 300. Specifically, using a more rigid material for the struts 636 provides increased rigidity and stability of the retractor 600 such that the retractor 600 maintains its geometry during the retraction procedure and maintains the retractor 600 in position relative to the installed pedicle screws. Consequently, the pedicle screws are also inhibited from movement away from their selected installation position. That is, the selected distance between the pedicle screws remains substantially constant throughout the surgical procedure.

In a further embodiment of the present disclosure, the minimally open retraction device or retractor is illustrated in FIGS. 6A-6B and referenced as 700. The retractor 700 includes first and second blades 710, 720. The blades 710, 720 include proximal portions 712, 722 and distal end portions 714, 724. The distal end portions 714 of the blade 710 are spaced apart from one another and define an arcuate cut-out 713. Similarly, the distal end portions 724 of the blade 720 are spaced apart from one another and define an arcuate cut-out 723. Each blade 710, 720 includes a pair of feet 716, 726 attached to the respective distal end portions 714, 724. The feet 716, 726 extend away from the arcuate cut-outs 713, 723 and are substantially orthogonal to a plane defined by the respective blades 710, 720. Each foot 716, 726 has a hole 702 extending therethrough. The holes 702 may be circular, elliptical, or oblong. When the holes 702 of blade 710 are aligned with the holes 702 of blade 720, the arcuate cut-outs 713, 723 define an opening 732 that permits access to the operative site similar to the opening 632 discussed with respect to the retractor 600. In this embodiment, the blades 710, 720 are formed from materials that were previously discussed with regards to the retractor 100.

Alternatively, as seen in FIGS. 7A and 7B, the minimally open retraction device or retractor may be formed as an integral unit that is referenced as 800. The retractor 800 includes blades 710, 720 having respective proximal ends 712, 722. The blades 710, 720 include distal end portions 714, 724. The distal end portions 714, 724 are connected at their ends, thus the retractor 800 is an integrated device. The distal end portions 714 of the blade 710 are spaced apart from one another and define an arcuate cut-out 713. Similarly, the distal end portions 724 of the blade 720 are spaced apart from one another and define an arcuate cut-out 723. The arcuate cut-outs 713, 723 cooperatively define an opening 832 that extends through the retractor 800 and permits access through the retractor 800 to the operative site similar to the opening 632 of retractor 600. A pair of feet 816 is attached to the region where the distal end portions 714, 724 join together. The feet 816 extend outwards from the opening 832 and include a hole 802. The blades 710, 720 can be manipulated by the practitioner towards each other (FIG. 7B) such that the retractor 800 is in a first condition and ready to be inserted into a minimal incision in the patient's skin. Once the retractor 800 is installed through the skin and into the operative site, the blades 710, 720 may be spread apart (i.e. a second condition) as previously discussed in detail hereinabove with respect to the retractor 600.

Figure 9:
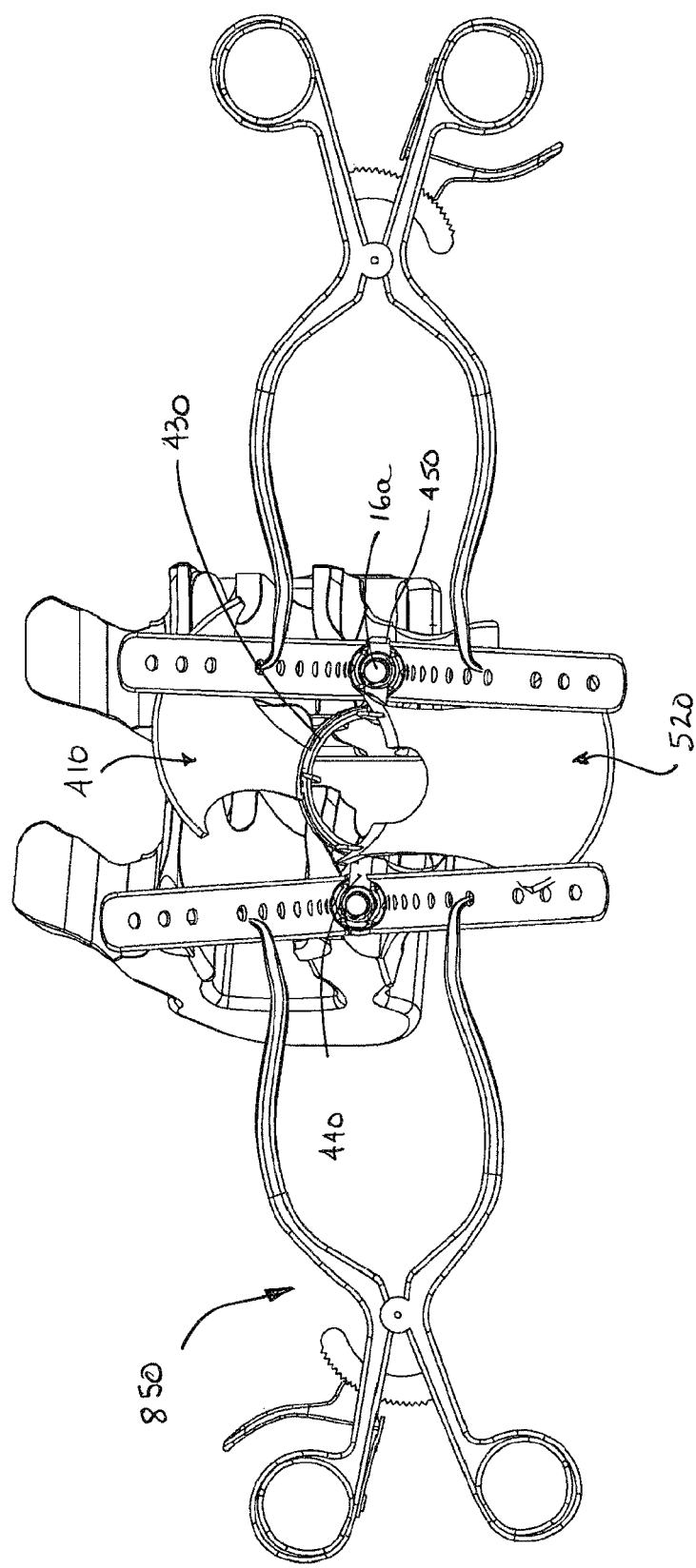
FIG. 9 is a top perspective view of the minimally open retraction device of FIG. 4E installed onto a pair of pedicle screws.

Referring now to FIGS. 8 and 9, in conjunction with FIG. 4E, a method of using the retractor 500 is disclosed. A method and supporting structures for using the retractor 500 are disclosed in U.S. patent application Ser. No. 11/528,223, filed on Sep. 26, 2006, owned by the assignee of the present application, the entire contents of which are hereby incorporated by reference. An example of a temporary set screw 16a is illustrated in FIG. 8. The temporary set screw 16a includes threads 18a at a distal end thereof. The threads 18a are adapted to engage corresponding thread structures in the head 12 of the pedicle screw 10 (FIG. 1C). At the opposing end of the temporary set screw 16a is a head that is adapted to engage driving tools as are known in the art.

Initially, the practitioner installs a pair of pedicle screws 10 using known open or mini-open surgical techniques and instruments. Alternatively, percutaneous placement of the pedicle screws 10 is contemplated by any suitable technique. In this regard, the methods and devices of the aforementioned U.S. patent application Ser. No. 11/528,223 may be particularly useful if the pedicle screws 10 are installed percutaneously in the selected locations, with an incision made through the patient's skin such that the incision spans the distance between the pedicle screws. The practitioner then dissects a minimum amount of tissue between the pedicle screws 10 and installs an arcuate member 430 therebetween. The arcuate member 430 includes rod portions 440, 450 that are received in the channels 14 of the pedicle screws 10. Subsequently, a pair of temporary set screws 16a is installed into the heads 12 of the pedicle screws 10 and secure the arcuate member 430 in its desired position. By securing the arcuate member 430 to the pedicle screws 10, the relative position of the pedicle screws 10 to each other is maintained throughout the surgical procedure.

Alternatively, the practitioner may substitute a different retractor for retractor 500. For example, the retractor 700 is installed by inserting one of the blades 710, 720 into the incision such that the shafts of the temporary set screws 16a pass through the holes 702. Once the first blade is installed, the remaining blade is installed in the same manner. With the blades 710, 720 installed in the operative site, the practitioner spreads the blades 710, 720 apart from one another and retracts tissue surrounding the operative site. The practitioner may grasp the blades 710, 720 and retract the tissue or may use a conventional retractor, such as a Gelpi retractor 850, to move the blades 710, 720. Alternately, the practitioner may select the retractor 800 for the procedure. In this instance, the practitioner inserts the retractor 800 into the incision and positions the retractor 800 such that the holes 802 are aligned with the temporary set screws 16a. Moving the retractor 800 towards the pedicle screws 10 couples the retractor 800 to the pedicle screws 10 by inserting the shafts of the temporary set screws 16a through the holes 802 of the retractor 800. The practitioner then manually separates the blades 810, 820 of the retractor 800 and retracts tissue surrounding the operative site. After the tissue is retracted, the practitioner may perform procedures on the accessible region such as a diskectomy, rod stabilization, prosthetic installation, etc.

Additionally, the minimally invasive retraction structures disclosed in U.S. patent application Ser. No. 11/528,223 may be used in conjunction with either retractor 700 or retractor 800. In this configuration, incisions and openings are created in the patient's skin using known techniques. The pedicle screws 10 are then installed in their desired locations. The pedicle screws 10 may be installed prior to installing the minimally invasive retractors 60 or they may be installed as an assembled unit. Once the minimally invasive retractors 60 are installed over the pedicle screws 10, the practitioner either manually separates the blades to retract tissue surrounding the pedicle screw 10 or employs a conventional retractor (e.g. a Gelpi refractor) to separate the blades and retract tissue around the pedicle screw 10. Once the tissue around the pedicle screws 10 is retracted, the practitioner then makes an incision between the pedicle screws 10 and dissects a minimally open region for inserting the arcuate member 830. Once the arcuate member is positioned, the practitioner performs the steps previously discussed.

Each of the presently disclosed embodiments provides a retractor that can be inserted through a minimal opening. In addition, the retractors are reconfigurable after installation such that the practitioners can retract tissue surrounding the operative site. The presently disclosed embodiments of the retractor also include orifices on the blades that are configured for cooperating with a convention retraction instrument such as a Gelpi retractor. Further still, the retractors provide an access opening for inserting or removing various instruments, prosthetics, or tissue. In conjunction with the above, pedicle screws may be installed and act as anchors points for the retractors and further increasing the options available to the practitioner during surgical procedures.

In each of the disclosed embodiments, a funnel-shaped access opening is defined which is wider at the proximal, skin level of the incision and narrower at the bottom, or lower section of the incision where the retractor is fixed in position relative to the pedicle screws. Contrary to prior devices which attempt to create an access opening of the reverse shape, i.e., a narrower opening at the skin level and a widened section below the skin adjacent the working area on the facets and interbody space, the access opening of the present devices provides improved visibility of the operative site and the widened top section allows insertion and removal of instruments and accessories (e.g., light, suction, irrigation) without interfering with surgical instruments already inserted into the opening and which the surgeon desires to leave in place despite also desiring to introduce other accessories as mentioned above. The fixation of the lower portion of the retractor structure to the set screw is important, as the narrower end of the funnel-shaped retractor is maintained in the desired position relative to the anatomy to be operated upon.

It will be understood that various modifications may be made to the embodiments of the presently disclosed minimally open retraction devices or retractors. Therefore, the above description should not be construed as limiting, but merely as exemplifications of embodiments. Those skilled in the art will envision other modifications within the scope and spirit of the present disclosure.

What is claimed is:

1. A surgical retraction device comprising:
a first blade positionable on a first side of a vertebral body;
a second blade positionable on a second side of the vertebral body and laterally spaced from the first blade and defining a gap therebetween, the second blade being flexible such that the gap between the first and second blades is variable;
a first foot coupled to a distal end of the surgical retraction device, the first foot having a first hole therethrough and attachable to a first pedicle screw;
a second foot coupled to the distal end of the surgical retraction device, the second foot having a second hole therethrough and attachable to a second pedicle screw, the first blade flexibly coupled to the first foot and the second blade flexibly coupled to the second foot, the second foot longitudinally spaced from the first foot and defining a gap therebetween; and
an opening located at the distal end of the surgical retraction device, the opening at least partially defined by the first and second feet.

2. The surgical retraction device of claim 1, wherein the first and second blades are made from a suitable biocompatible material.

3. The surgical retraction device of claim 1, further including orifices on the first and second blades, the orifices configured to cooperate with a surgical retraction instrument.

4. The surgical retraction device of claim 1, wherein distal portions of the first and second blades define arcuate cutouts.

5. The surgical retraction device of claim 1, further including a third foot and a fourth foot, the first and third feet attached at a distal end of the first blade, the second and fourth feet attached at a distal end of the second blade.

6. The surgical retraction device of claim 5, wherein the first and second feet extend away from the opening in opposite directions.

7. The surgical retraction device of claim 5, wherein the third and fourth feet extend away from the opening in opposite directions.

8. The surgical retraction device of claim 7, further including set screws, wherein the first and second blades are coupled to pedicle screws using the set screws installed into heads of the pedicle screws, the set screws including shafts that pass through the first and second holes in the first and second feet.

9. The surgical retraction device of claim 1, wherein the first foot is longitudinally and laterally spaced from the second foot.

10. The surgical retraction device of claim 1, wherein the first foot is coupled to a distal end portion of the first blade and the second foot is coupled to a distal end portion of the second blade.

11. A surgical retraction device comprising:
a first blade;
a second blade, the second blade connected to the first blade at distal ends of the first and second blades, the surgical retraction device being monolithic;
an opening extending through a distal portion of the surgical retraction device, the opening defined by distal portions of the first and second blades; and
a first foot and a second foot coupled to a distal end of the surgical retraction device, the first foot having a first hole therethrough for receiving a portion of a first set screw, the second foot having a second hole therethrough for receiving a portion of a second set screw, the first foot attachable to a first pedicle screw and the second foot attachable to a second pedicle screw using the first and second set screws, the first and second feet longitudinally and laterally spaced apart, wherein the first and second feet are orthogonal to the first and second blades when the first and second blades are parallel to each other.

12. The surgical retraction device of claim 11, wherein the surgical retraction device is made from a suitable biocompatible material.

13. The surgical retraction device of claim 11, further including orifices on the first and second blades, the orifices configured to cooperate with a surgical retraction instrument.

14. The surgical retraction device of claim 11, wherein the distal portions of the first and second blades define arcuate cut-outs.

15. The surgical retraction device of claim 11, wherein the opening permits access to an operative site.

16. The surgical retraction device of claim 15, wherein the first and second feet extend away from the opening in opposite directions.

17. The surgical retraction device of claim 11, wherein the opening extends from the distal portion of the first blade to the distal portion of the second blade.

18. The surgical retraction device of claim 11, wherein the first and second feet are coupled to respective distal portions of the first and second blades.

19. The surgical retraction device of claim 11, wherein the first and second blades are resilient.

20. A surgical retraction device comprising:
a first blade;
a second blade laterally spaced from the first blade and defining a gap therebetween, the second blade being flexible such that the gap between the first and second blades is variable;
a first foot coupled to a distal end of the surgical retraction device, the first foot having a first hole therethrough and attachable to a first pedicle screw;
a second foot coupled to the distal end of the surgical retraction device, the second foot having a second hole therethrough and attachable to a second pedicle screw, the first blade flexibly coupled to the first foot and the second blade flexibly coupled to the second foot;
first and second set screws, the first and second blades attachable to the first and second pedicle screws using respective first and second set screws installed into heads of the first and second pedicle screws, the first and second set screws including shafts that pass through the first and second holes in the first and second feet; and
an opening located at the distal end of the surgical retraction device, the opening at least partially defined by the first and second feet.

* * * * *